US012093460B2

(12) United States Patent
Yetkin et al.

(10) Patent No.: US 12,093,460 B2
(45) Date of Patent: Sep. 17, 2024

(54) SYSTEMS, APPARATUSES AND METHODS FOR CONTROLLING PROSTHETIC DEVICES BY GESTURES AND OTHER MODALITIES

(71) Applicant: Board of Regents, The University of Texas System, Austin, TX (US)

(72) Inventors: Oguz Yetkin, Dallas, TX (US); Joseph D. Sanford, Dallas, TX (US); Dan O. Popa, Louisville, KY (US); Lena C. Wallace, Grand Prairie, TX (US); Fahad Mirza, Arlington, TX (US); Roopak Karulkar, Arlington, TX (US); Sumit Kumar Das, Louisville, KY (US); Joshua R. Baptist, Louisville, KY (US); J. Paul Carpenter, Fort Worth, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 333 days.

(21) Appl. No.: 17/106,478

(22) Filed: Nov. 30, 2020

(65) Prior Publication Data
US 2021/0181855 A1    Jun. 17, 2021

Related U.S. Application Data

(63) Continuation of application No. 15/488,500, filed on Apr. 16, 2017, now Pat. No. 10,852,835.
(Continued)

(51) Int. Cl.
*G06F 3/01* (2006.01)
*A61F 2/70* (2006.01)
(Continued)

(52) U.S. Cl.
CPC ............... *G06F 3/017* (2013.01); *A61F 2/72* (2013.01); *G06F 1/163* (2013.01); *G06F 3/014* (2013.01);
(Continued)

(58) Field of Classification Search
CPC .... A61F 2/72; A61F 2/583; A61F 2002/7615; A61F 2002/7625; A61F 2002/762; G06F 3/017; G06F 3/0308
See application file for complete search history.

(56) References Cited

U.S. PATENT DOCUMENTS 6,344,062 B1    2/2002  Abboudi et al.
9,939,899 B2    4/2018  Allec et al.
(Continued)

FOREIGN PATENT DOCUMENTS

KR    20090076710 A  *  9/2008
WO    WO-2015170112 A1 * 11/2015 ............. A61F 2/583

OTHER PUBLICATIONS

Advisory Action corresponding to U.S. Appl. No. 15/488,500 dated Jun. 27, 2019.
(Continued)

*Primary Examiner* — Christie Bahena
(74) *Attorney, Agent, or Firm* — Jenkins, Taylor & Hunt, P.A.

(57) ABSTRACT

Systems and methods for manual gesture recognition to control prosthetic devices. Low encumbrance systems utilizing glove-based recognition to control prosthetic devices. Prosthetic control systems and methods are also provided utilizing elements for application on the user's fingernails.

15 Claims, 14 Drawing Sheets

Related U.S. Application Data

(60) Provisional application No. 62/323,592, filed on Apr. 15, 2016.

(51) Int. Cl.
    *A61F 2/72*     (2006.01)
    *G06F 1/16*     (2006.01)

(52) U.S. Cl.
    CPC ........ *G06F 3/015* (2013.01); *A61F 2002/704* (2013.01); *A61F 2002/705* (2013.01); *A61F 2002/707* (2013.01)

(56) References Cited

U.S. PATENT DOCUMENTS

| | | | |
|---|---|---|---|
| 10,852,835 | B2 | 12/2020 | Yetkin et al. |
| 2008/0136775 | A1* | 6/2008 | Conant ............... G06F 3/014 345/156 |
| 2008/0215162 | A1 | 9/2008 | Farnsworth et al. |
| 2010/0225449 | A1* | 9/2010 | Hartmann .......... G06K 19/0675 340/10.4 |
| 2010/0231505 | A1 | 9/2010 | Iwata |
| 2012/0139708 | A1* | 6/2012 | Paradiso ............. G06F 3/0346 340/10.1 |
| 2013/0041477 | A1* | 2/2013 | Sikdar ................ A61F 2/583 623/57 |
| 2015/0357948 | A1* | 12/2015 | Goldstein .......... G05D 7/0676 318/16 |
| 2016/0084650 | A1 | 3/2016 | Hsu et al. |
| 2017/0031453 | A1 | 2/2017 | Presura |
| 2017/0296363 | A1 | 10/2017 | Yetkin et al. |

OTHER PUBLICATIONS

Frigyes, Gary (2015) "Fundamentals of Photoelectric Sensors," Automation.com Library, date verified by wayback machine on Apr. 21, 2015.

Kim et al. (2012) "Digits: Freehand 3D Interactions Anywhere Using a Wrist-Worn Gloveless Sensor," conference paper, pp. 167-176.

Laviola et al. (undated) "Flex and Pinch: A Case Study of Whole Hand Input Design for Virtual Environment Interaction," Brown University, pp. 1-5.

MAMIT (2015) "CES 2015: The 'Ring' to Control Them All? How Logbar Gesture Control Ring Works," Techtimes.com (accessed Jan. 19, 2016).

Notice of Allowance corresponding to U.S. Appl. No. 15/488,500 dated Jul. 8, 2020.

Office Action (Restriction Requirement) corresponding to U.S. Appl. No. 15/488,500 dated May 15, 2018.

Office Action corresponding to U.S. Appl. No. 15/488,500 dated Oct. 2, 2018.

Office Action corresponding to U.S. Appl. No. 15/488,500 dated Mar. 6, 2019.

Office Action corresponding to U.S. Appl. No. 15/488,500 dated Feb. 27, 2020.

Olewitz (2015) "Type on an Invisible Keyboard with the Gest Motion-Control Glove," DigitalTrends.com (accessed Jan. 19, 2016).

Sanford et al. (undated) "A Novel EMG-Free Prosthetic Interface System Using Intra-Socket Force Measurement and Pinch Gestures," University of Texas—Arlington.

Sanford et al. (2015) "Surface EMG and Intra-Socket Force Measurement to Control a Prosthetic Device," Proceedings of SPIE, vol. 9494, University of Texas—Arlington.

Sanford et al. (2017) "Concurrent Surface Electromyography and Force Myography Classification During Times of Prosthetic Socket Shift and User Fatigue," Journal of Rehabilitation and Assistive Technologies Engineering. vol. 4, pp. 1-13.

Touch Bionics pamphlet (2014) "my i-limb™ App: Quick Reference Guide for i-limb™ Access," Touch Bionics Inc. (www.touchbionics.com).

Yetkin et al. (2015) "Control of a Powered Prosthetic Hand via a Tracked Glove," Journal of Mechanical Design, vol. 9, No. 2.

Yetkin et al. (2015) "Control of a Powered Prosthetic Device via a Pinch Gesture Interface," Proceedings of SPIE, vol. 9494, University of Texas—Arlington.

Yetkin et al. (2016) "An Extremely Lightweight Fingernail Worn Prosthetic Interface Device," Proceedings of SPIE, vol. 9859, University of Texas—Arlington.

Yetkin et al. (undated) "Evaluation of Prosthetic Control via Hand and Gesture Tracking," University of Texas—Arlington.

* cited by examiner

GESTURE 1

GESTURE 2

GESTURE 3

GESTURE 4

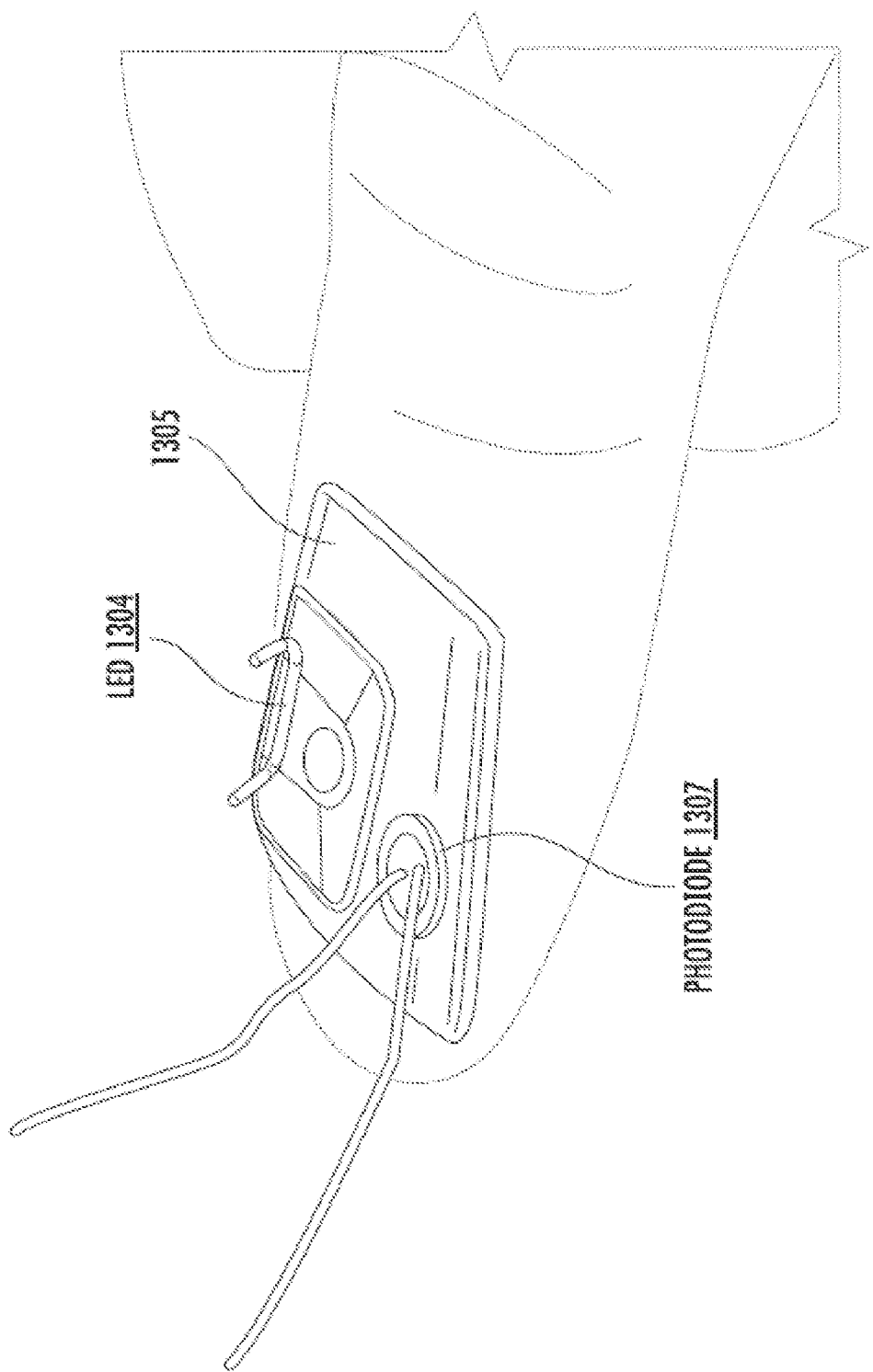

SYSTEMS, APPARATUSES AND METHODS FOR CONTROLLING PROSTHETIC DEVICES BY GESTURES AND OTHER MODALITIES

RELATED APPLICATIONS

This application is a continuation of U.S. patent application Ser. No. 15/488,500, filed Apr. 16, 2017, which itself claims priority from U.S. Provisional Application Ser. No. 62/323,592, filed Apr. 15, 2016, the entire disclosure of which is incorporated herein by this reference.

GOVERNMENT INTEREST

This invention was made with government support under Grant No. # NRI IIS-1208623 awarded by National Science Foundation. The government has certain rights in the invention.

TECHNICAL FIELD

This disclosure relates generally to systems and methods in the field of wearable electronics and human control interfaces. More specifically, the disclosure relates to techniques for recognizing signals to control powered prosthetic devices providing extended freedom of motion and optional modalities of operation.

BACKGROUND

The state of the art for commercial robotic prosthetic systems is to use a pair of electromyography (EMG), also referred to as surface electromyography (SEMG), sensors on the residual limb. These sensors detect the electrical activity of the muscles in the user's remaining limb during muscle activation. For prosthetic hand devices, grasp patterns are typically selected by scrolling through "menus" by co-contracting different muscles (e.g., biceps and triceps) and putting the prosthetic device in different operating modes. Some systems also allow grasp selection via apps running on a smart phone.

Conventional prosthetic systems allow users to regain some lost functionality, but in a limited way. For example, prosthetic hand devices typically allow the user limited "open" or "close" functionality. While current powered prosthetic devices boast multiple degrees of freedom and dexterity levels that allow a user to perform a number of operations and movements, interaction with these devices is still limited, and limiting, outside of the clinical setting. EMG data acquisition is highly variable and subject to noise due to linear distances along the surface of the skin above the sensed muscle. Perspiration and user fatigue can also cause degraded device performance.

The use of glove devices as an input interface has been demonstrated extensively in virtual reality environments. In the last few decades the gaming industry has used glove devices for glove-based input. Although some research has been done relating to the use of glove devices in other fields, none has exclusively focused on the control of powered prosthetic devices.

Accordingly, a need remains for improved low encumbrance systems and methods for controlling powered prosthetic devices.

SUMMARY

Embodiments of the present invention provides systems, apparatuses, and methods for recognizing (e.g., finger or hand) gestures and controlling external (e.g., prosthetic hand) devices based on the recognition of the gestures.

According to a first aspect of the invention, there is provided a system comprising a signal element configured for disposal on a first finger of a user; and a detection element configured for disposal on a second finger of a user, and configured to detect a signal generated by the signal element, wherein the signal indicates that a gesture has been performed using the user's fingers.

According to a second aspect of the invention, there is provided a system comprising a plurality of conductive thimbles configured for disposal on a user's fingers, the user's fingers being fingers of a first arm of the user, wherein the conductive thimbles are configured to output a signal representing a gesture performed with the user's fingers.

According to a third aspect of the invention, there is provided a system, comprising a glove configured to be worn on a user's first hand, the user's first hand being a hand of a first arm of the user, wherein the glove is configured to output a signal indicating a gesture performed with the user's first hand.

According to a fourth aspect of the invention, there is provided a method comprising outputting a signal corresponding to a gesture; and controlling a prosthetic device based on the outputted signal, whereby the prosthetic device is controlled based on the gesture.

Other systems, apparatuses, and methods are also provided.

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

FIG. 13 is an image of a gesture recognition and control system disposed on a user's hand, according to some embodiments.

NOTATION AND NOMENCLATURE

Figure 1:
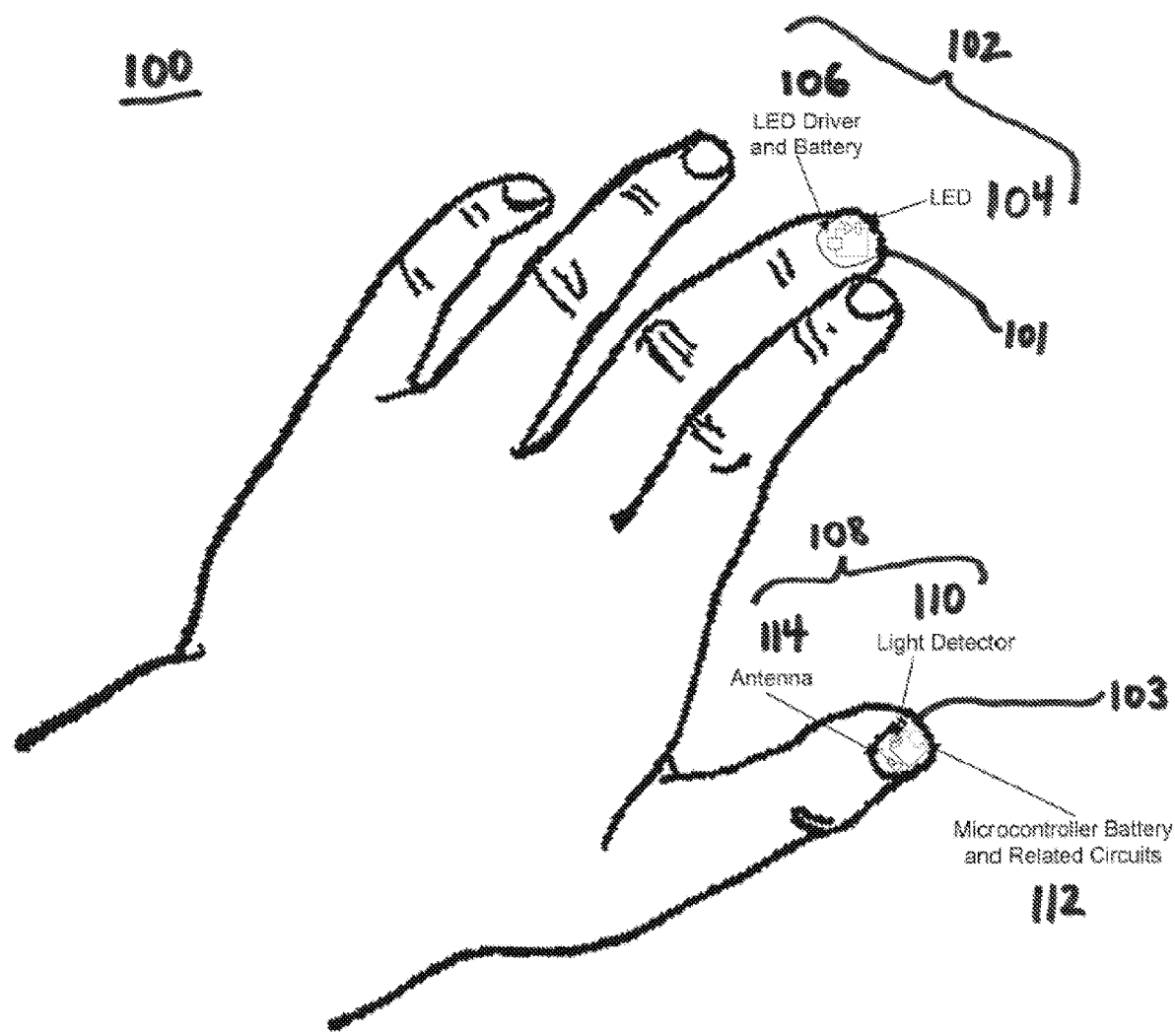
FIG. 1 is a schematic drawing of a manual gesture recognition and control system disposed on a user's hand, according to some embodiments.

Certain terms are used throughout the following description and claims to refer to particular system components and configurations. As one skilled in the art will appreciate, the same component may be referred to by different names. This document does not intend to distinguish between components that differ in name but not function. In the following discussion and in the claims, the terms "including" and "comprising" are used in an open-ended fashion, and thus should be interpreted to mean "including, but not limited to . . . "

Various terms are now explained, although their meanings may be more easily grasped upon reading of the full detailed description set forth below in conjunction with the explanation given here. The term "pinch gesture," as used herein, is explained as follows. A pinch gesture is a manual gesture that is performed by bringing together or touching together (e.g., to each other, to one or more other finger(s), or to another part of the hand) one or more fingers on the hand being used for input. Such a gesture can be used to actuate an external device, such as a robotic prosthetic limb (e.g., a hand worn on the user's other arm), a music player, a machine, etc. Many different gestures can be defined and used to cause respective different operations to be performed on an external device. For example, a finger pad of one finger may be touched to or brought together with a finger pad of another finger, a finger pad of one finger may be touched to or brought together with a fingernail of another finger, finger pads of two fingers may be touched to or brought together with a finger pad of another finger, and so on. In some aspects of the invention, pinch gestures include gestures performed by bringing together or touching together two or more fingers, or touching the fingers to various parts of the hand, such as different locations on the palm. Thus, a pinch gesture may but need not involve pinching in the ordinary sense of the term. As will be understood by one of ordinary skill in the art, embodiments described herein may apply to finger and hand (manual) gestures generally. The speed and frequency of the gestures (such as a double-tap, analogous to a mouse double-click or a longer-than-normal gesture, analogous to a long-press on a touch screen) can also be used to distinguish user intent. As used herein, the terms "recognition" and "tracking" may be interchanged.

It should also be noted that in the instant disclosure the term "finger" may refer to any finger, including the thumb. It is also noted that in the instant disclosure the term "light" may refer to but is not limited to the visible spectrum. The instant disclosure makes reference to detecting various characteristics of a signal, e.g., a frequency; a color; an RFID tag ID; a signal intensity, strength, or amplitude, or a change in one of these; a timing; a resonant frequency of a circuit transmitting or generating the signal; and a frequency or pulse pattern. All of these characteristics and the like may be referred to as "characteristics" of the signal. The term "timing" of the signal may refer to any time aspect of the signal detected, such as a time of reception or transmission of the signal (e.g., relative to time of transmission of an interrogation signal triggering the signal as a response signal from the signal element), a characteristic response time for a given finger, or any other time characteristic of the signal discussed herein.

The instant disclosure uses the term "characteristics" of a gesture to refer to various characteristics of a gesture, such as a particular finger or fingers used, a particular position of one or more fingers, a particular pose or grasp pattern/grip pattern of one or more fingers, a particular movement performed by one or more fingers, and a state of contact or non-contact of one or more fingers with another one or more fingers or with another part of the hand. By "a particular finger or fingers used" is meant an indication or identification of which particular finger(s) are being used in the performance of the gesture. Further, the instant disclosure refers to a controller controlling a prosthetic device based on a detected signal (corresponding to a gesture). In some cases, such control may be performed directly by the controller, while in other cases such control may be performed indirectly by the controller, that is, via one or more intermediate devices, such as another computer device. The instant disclosure also refers to a signal representing muscle force or pressure; this locution may refer also to a signal representing a change in muscle force. And more generally, as will be understood by one of ordinary skill in the art upon reading the instant disclosure, in some cases the disclosure may refer to detecting a quantity as a shorthand for detecting either the quantity or a change in the quantity (the quantity being a signal or a characteristic of a signal being detected, such as the frequency or amplitude of an electrical signal, light, etc.). Finally, the instant disclosure may refer to causing a prosthetic device to perform an action as a shorthand for causing a prosthetic device to perform an action, change position or move in a certain manner (e.g., a manner corresponding to a detected signal/recognized gesture); in other words, in this context, 'performing an action' may but need not refer to changing position or moving in a certain manner.

DETAILED DESCRIPTION

The foregoing description of the figures is provided for the convenience of the reader. It should be understood, however, that the embodiments are not limited to the precise arrangements and configurations shown in the figures. Also, the figures are not necessarily drawn to scale, and certain features may be shown exaggerated in scale or in generalized or schematic form, in the interest of clarity and conciseness. The same or similar parts may be marked with the same or similar reference numerals.

While various embodiments are described herein, it should be appreciated that the present invention encompasses many inventive concepts that may be embodied in a wide variety of contexts. The following detailed description of exemplary embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. The scope of the invention is defined by the appended claims and equivalents thereof.

Illustrative embodiments of the invention are described below. In the interest of clarity, not all features of an actual implementation are described in this specification. In the development of any such actual embodiment, numerous implementation-specific decisions may need to be made to achieve the design-specific goals, which may vary from one implementation to another. It will be appreciated that such a development effort, while possibly complex and time-consuming, would nevertheless be a routine undertaking for persons of ordinary skill in the art having the benefit of this disclosure.

Figure 2:
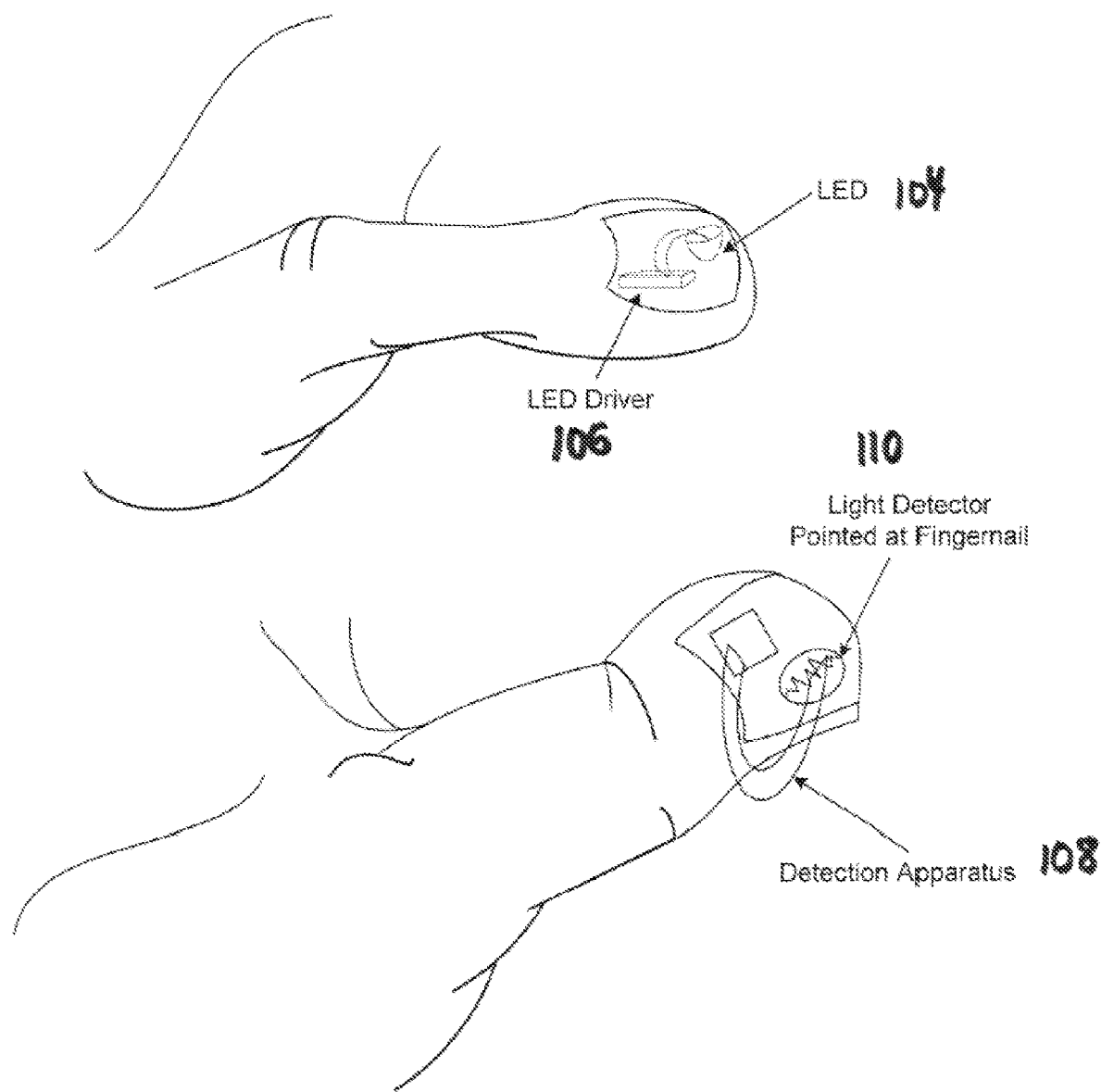
FIG. 2 is a schematic drawing of a pinch gesture performed with a gesture recognition and control system disposed on a user's hand, according to some embodiments.

FIG. 1 illustrates a system 100 for recognizing pinch gestures and controlling a prosthetic device based on the recognized gestures, according to an embodiment. (A system for recognizing gestures and controlling a prosthetic device based on the recognized gestures may be referred to as a gesture recognition and control system.) In this embodiment, all recognition components of system 100 are disposed on the user's fingernails 101. As illustrated in FIG. 1, a signal element 102 comprising an LED 104 is disposed on the user's fingernail 101. The signal element 102 is configured with one or more LEDs 104 and LED driver circuitry 106 (including batteries). A detection element 108 is disposed on the user's thumbnail 103. The LED signal element 102 is positioned facing the fingertip or fingernail, to transmit light such that the detection element 108 (in this case on the thumb) detects the light when a pinch gesture is performed as shown in FIG. 2. (FIG. 2 intends to show a case of bringing the finger pad to touch the thumb pad.) In other embodiments, it's also possible to point a light detector away from the fingernail, allowing for the performance of a second type of pinch gesture by touching the finger pad to the thumbnail, instead of touching the finger pad to the thumb pad. Although FIG. 1 shows only one finger provided with a signal element 102, all four fingers can be equipped with individual signal elements 102 (see, e.g., the embodiment of FIG. 3). In other embodiments, the detection element 108 may be disposed on another finger, instead of the thumb, with the signal element(s) 102 on the other finger(s) appropriately positioned for signal alignment.

For embodiments implemented with signal elements 102 disposed on more than one finger, the individual LED signal elements 102 can be modulated or pulsed at a frequency specific to each finger. The color of the LED 104 may also be chosen so that it can transmit through 1-3 cm of tissue (generally red or infrared) at a reasonable intensity. The user performs a gesture by bringing together or touching one or more fingers equipped with a signal element 102 to the finger containing the detection element 108. Light from the LED signal element 102 traverses the fingers and is detected by the detection element 108.

The LED-based detection element 108 comprises a light detector 110 (e.g., a photodiode, photoresistor) and microcontroller circuitry 112 (including a battery) to detect which finger or fingers are in close proximity or in contact with the finger on which the detection element 108 is mounted. The LED-based system 100 takes advantage of the fact that certain frequencies of light are transmitted through human tissue. Several methods can be used to distinguish between different signal elements 102/fingers, including but not limited to pulsing the signal elements 102 at different frequencies, choosing LEDs 104 or a combination of LEDs 104 on each finger of slightly different colors (infrared, red, yellow, etc.), or using a mechanism on each signal element 102 which is triggered by a light pulse or a Radio Frequency (RF) pulse being emitted by the device on the approaching finger, which then responds by turning on the LED signal element 102. The detection element 108 is also configured with an antenna 114 to receive the signal transmitted by the signal element 102. The microcontroller 112 produces an output signal based on the signal received by the detection element 108. The output signal may be used, directly or indirectly, e.g. via a computer, to control an external device, such as a prosthetic device. The user may have one healthy arm and one disabled arm, and the user may use the healthy arm to wear the system 100 components (e.g., signal elements and detection elements) and perform the manual gestures, and the prosthetic device may be disposed on the user's disabled arm and may be controlled, via the system 100, by the gestures performed by the healthy arm. The control may involve causing the prosthetic device to perform an action, such as to take a certain position or pose, or move in a certain manner. The specific action performed, position/pose taken, or manner of movement would correspond to the specific gesture performed. Further description of this control of the prosthetic device based on the performed gestures is given elsewhere in this disclosure, and the description given here and elsewhere may apply to various embodiments even if that description is not provided together with those embodiments and not explicitly stated to be applicable to those embodiments, as will be understood by one of ordinary skill in the art. (More generally, it is noted that, for the sake of brevity, for some embodiments, not all elements of a gesture recognition and control system are described. For example, in some embodiments, description of the control of the external, e.g., prosthetic, device, including description of the microcontroller for producing output for performing that control based on the signal received by the detection element, is omitted. One of ordinary skill in the art will understand that, where the disclosure omits description of such functionality or structural elements for a given embodiment, the teachings pertaining to that functionality or structural element as included for other embodiments may be applicable to the embodiment for which the description of that element was omitted.)

Figure 3:
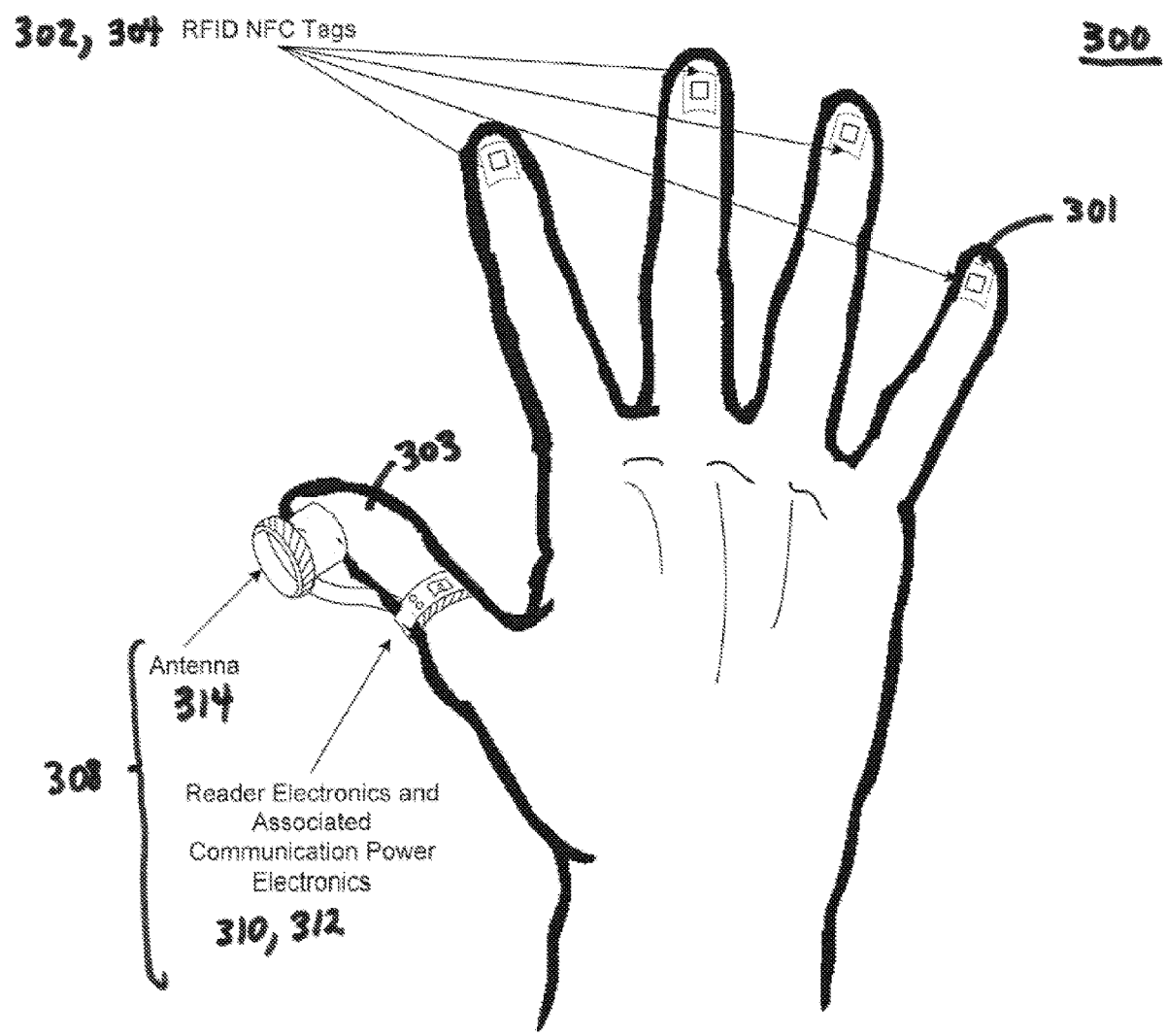
FIG. 3 is a schematic drawing of another manual gesture recognition and control system disposed on a user's hand, according to some embodiments.

FIG. 3 illustrates another gesture recognition and control system 300, according to an embodiment. In this embodiment, inductively coupled Radio Frequency Identification (RFID) tags 304 are disposed on the user's fingernails 301. The detection element 308 is a detachable ring fixture on the user's thumb 303, configured with a miniature RFID antenna 314, with associated electronics 310 to support tag reading, as well as electronics 312 to transmit information output, and power electronics. The signal elements 302 are the miniature RFID tags 304 disposed at the respective tips of the four fingers so that the detection element 308 on the thumb can discriminate which finger is nearest to the antenna 314 for subsequent pinch gesture recognition. Standard passive RFID tags (whether magnetically or electrically coupled) have individual unique IDs, in turn allowing for unique identification of the fingers without additional complexity. In some embodiments, magnetically coupled RFID tags may be optimal considering the short reading distances employed and the overall low power operation of such readers.

Various arrangements of antennas 314 and corresponding electronics 310, 312 are possible. For example, FIG. 3 shows a two-piece device including an antenna 314 disposed on the thumbnail and connected to a ring mounted on the thumb that contains the RF electronics 310 for interrogating the RFID tags 304 of the signal elements 302 and receiving responses from those RFID tags 304, and the microcontroller circuitry 312 for controlling an external device based on the received responses. The antenna 314 can be disposed on the thumbnail using any suitable means (e.g., direct adherence via an adhesive, via an elastic band wrapping around the fingertip to hold the antenna 314 in place for easy removal, etc.). Such implementations allow for positioning of the antenna 314 parallel the thumb. In other arrangements, the detection element 308, including both the antenna 314 and associated electronics 310 and 312, may be housed entirely within in the ring on the thumb (e.g., not on the thumbnail). The antenna 314 incorporated on the ring body may be perpendicular to the finger. In other arrangements, the antenna 314 may have any of various configurations and orientations/positions. Embodiments implemented with a detection element 308 having only one antenna/reader may not be feasible for triangulation and/or localization of the signal element tags 304. However, in the general case of RF circuitry, signal element tag identification is feasible given the reading proximity of the disclosed implementations. Additionally, planar distance may be measureable based on measured signal intensity or through adjustment of interrogating frequency amplitudes to obtain general distance information.

Figure 4:
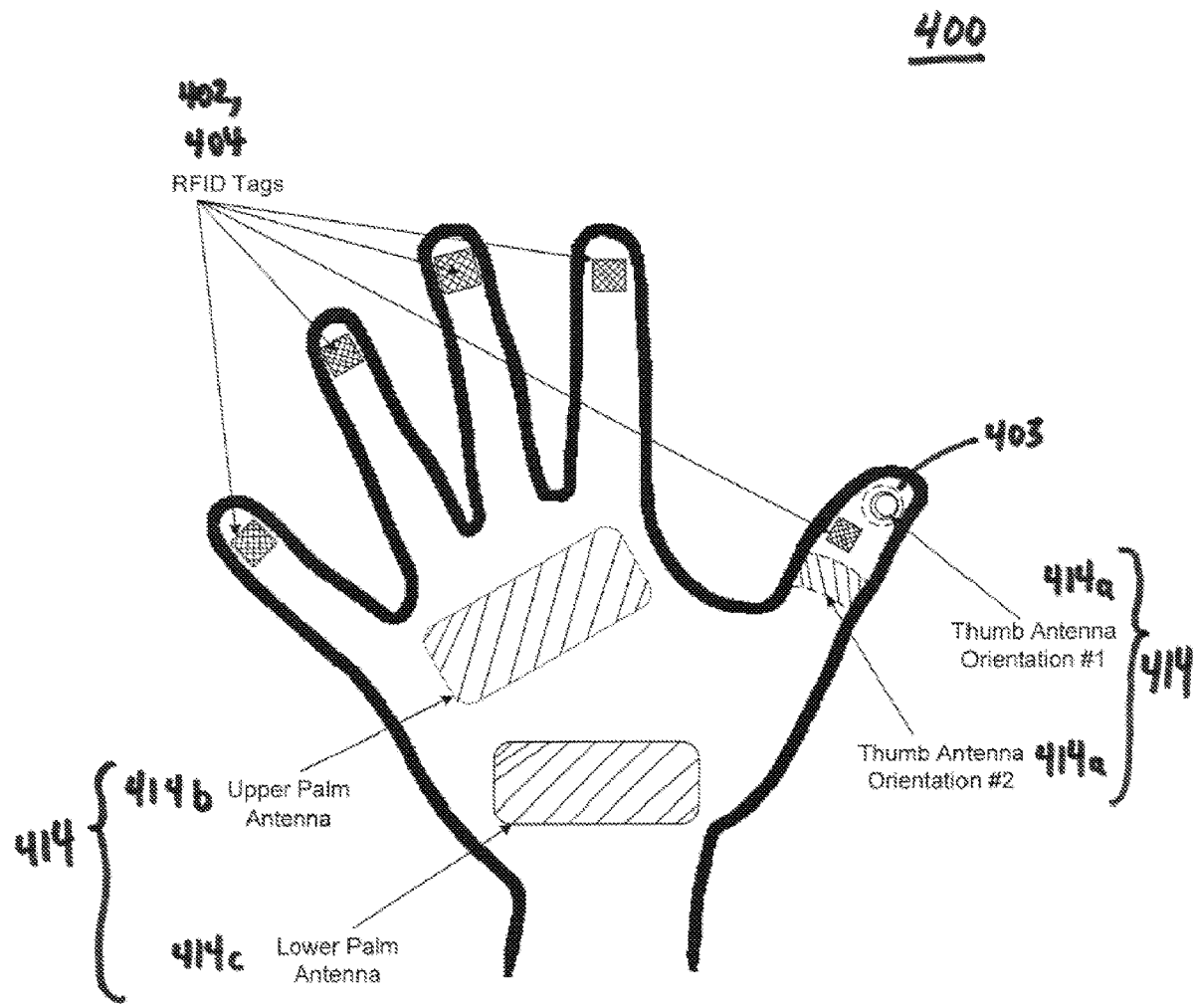
FIG. 4 is a schematic drawing of another manual gesture recognition and control system disposed on a user's hand, according to some embodiments.

FIG. 4 illustrates another gesture recognition and control system 400, according to an embodiment. In this embodiment, multiple signal elements 402 (each containing an RFID tag 404) and multiple detection elements are disposed on the user's hand. As shown in FIG. 4, a multiple antenna configuration is disclosed, including a plurality of antennas (collectively referred to as 414) on the user's hand, namely, a thumb antenna 414a located on the thumb, an upper palm antenna 414b located on the palm toward the fingers, and a lower palm antenna 414c located toward the wrist. Thumb antenna 414a may be disposed either on the thumbnail 403 (first orientation) or around the thumb (second orientation); in some arrangements, both of these thumb antennas 414a may be employed. With this configuration, one can spatially localize and triangulate the position of the signal element tag 404 in 3D space for further improved gesture recognition. By measuring signal intensity of the RFID tag 404 as acquired by a combination of the antennas and/or or by measuring the time between interrogation and data transmission (e.g., with synchronized or asynchronized electronics) between the antennas and tags, one can obtain a position of the RFID tag 404 in two dimensions (2D) relative to the plane of the palm as well as in three dimensions (3D). This can be accomplished in several ways. (For convenience, the controller and electronics, etc. associated with the antennas 414 are not shown in FIG. 4.)

One way is by triangulation based on signal intensity. This is based on the assumption that the attenuation of the signal by the surrounding fingers is negligible. For any RFID tag being queried, more than one sensor can be used to read the signal. The amplitude of the signal at each detector can be measured. The strength of the signal will correspond to the distance of the sensor to the RFID tag.

Another way is by triangulation based on time of flight. With sufficiently fast detectors, the time of arrival of the signal from the RFID tag can be measured accurately. Since the signal will arrive at a detector which is further away later than at a detector which is close by, the distance of the RFID tag to each sensor can be calculated. This will yield an approximation of the location.

In some embodiments, the two triangulation techniques described above can be combined with a model of the hand, adding geometrical constraints to the RFID tag location estimation. In another way, triangulation based on signal intensity can be combined with machine learning approaches to "train" a machine learning system (such as an Artificial Neural Network) with different "ground truth" hand poses and signal intensities as inputs. The system would learn to associate a combination of signal intensities for each RFID tag with a given hand pose. With a sufficiently large number of such training inputs, the system can learn to estimate hand poses without explicit knowledge of hand geometry or signal attenuation. In yet another way, triangulation based on signal intensity can be combined with Radio Frequency attenuation and propagation modeling, similar to approaches used in antenna design systems. Conventional commercial simulators which can model RF propagation may be used. Since the general shape of the hand and the poses it can achieve are well known, measured RF attenuation at each signal can be compared to what is theoretically expected for a variety of different poses, resulting in a pose estimate.

Embodiments along the lines of system 400 illustrated in FIG. 4 allow for the detection of additional gestures such as gestures used in sign language. Such embodiments may also be used to directly tele-operate a hand-like robotic manipulator, such as a prosthetic arm mounted contra-laterally, or an industrial robot. The triangulation techniques described above can also be implemented with other embodiments disclosed herein, including embodiments configured for light or sound signaling.

Figure 5:
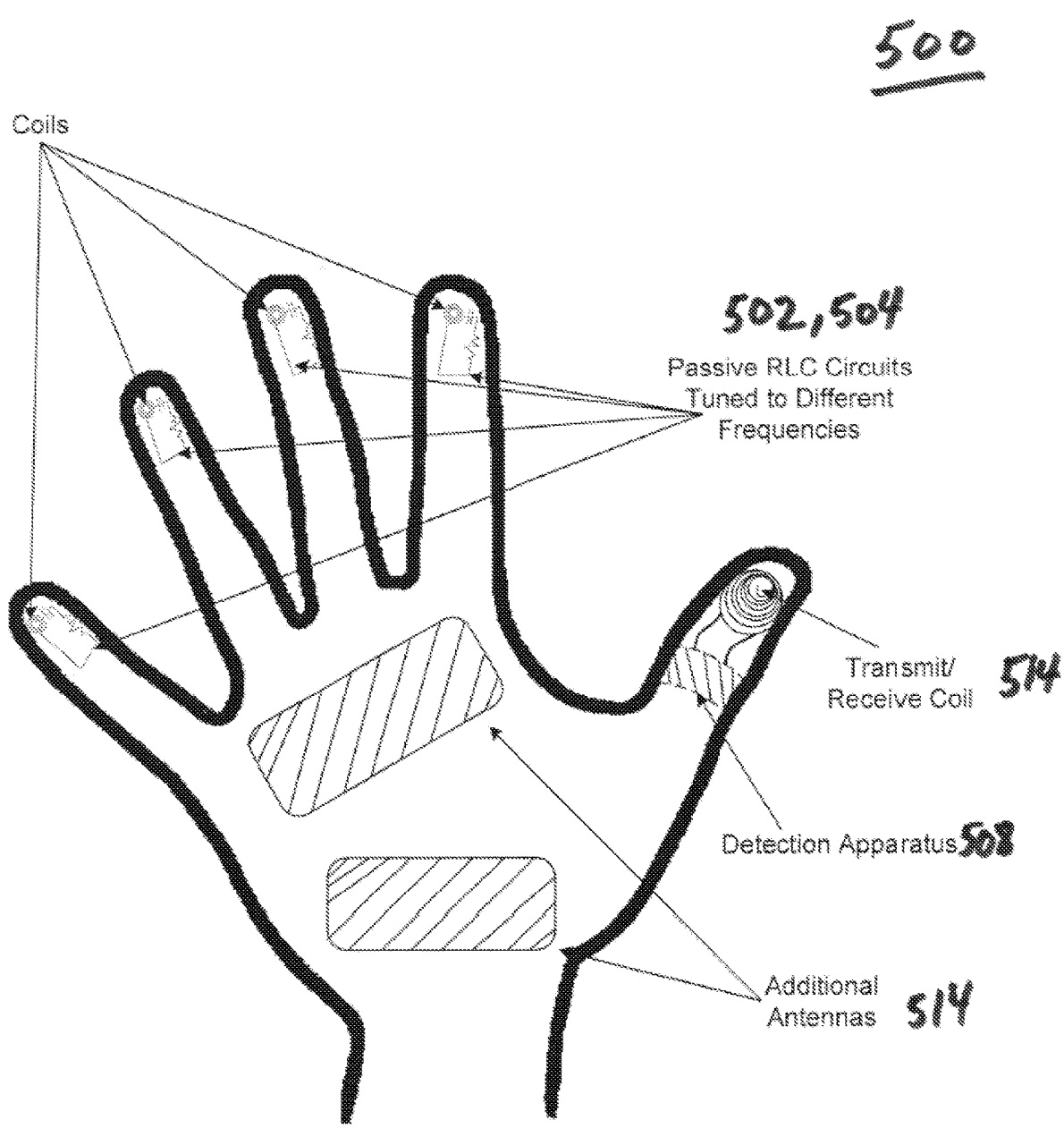
FIG. 5 is a schematic drawing of another manual gesture recognition and control system disposed on a user's hand, according to some embodiments.

FIG. 5 illustrates another gesture recognition and control system 500. This embodiment presents an alternative scheme for radio frequency interrogation for determining position and identity of the corresponding finger on which the circuit is placed. For signal elements 502, this implementation uses individually tuned LC resonant tank circuits 504 with an inductor (L) and a capacitor (C) placed in series. The circuit 504 is used as an electrical resonator, storing energy oscillating at the circuit's resonant frequency. Depending upon the pre-calculated specifications of the circuit 504, the circuit 504 can 'ring' or resonate when interrogated with the established resonant frequency. Some embodiments encompass the use of separately tuned signal elements 502 (one for each finger), and a detection element 508 with a transmitter and receiver, or a transceiver, such as a transmit/receive coil 514. Different methods for transceiving, or sending and receiving signals, may be used. One exemplary method comprises a voltage controlled oscillator to generate frequencies necessary to 'ring' or resonate the LC circuits 504. A software defined radio (a simplistic radio frequency (RF) spectrum analyzer) is used to read the signal being sent back by the LC circuit 504. For example, conventional software applications providing real-time signal spectral analysis may be used to determine the frequency of the signals output by the LC circuit 504. While FIG. 5 shows multiple antennas 514, some embodiments may be implemented with other antenna configurations and additional software defined radios. Various arrangements along the lines of FIG. 5 may allow for triangulation in 2D and 3D recognition. Other embodiments may be implemented incorporating detection elements 508 (which are also LC circuits) that are tuned to the resonant frequency of the signal element circuits 504 mounted on the fingers, using simple circuitry to measure the produced signals.

Figure 6:
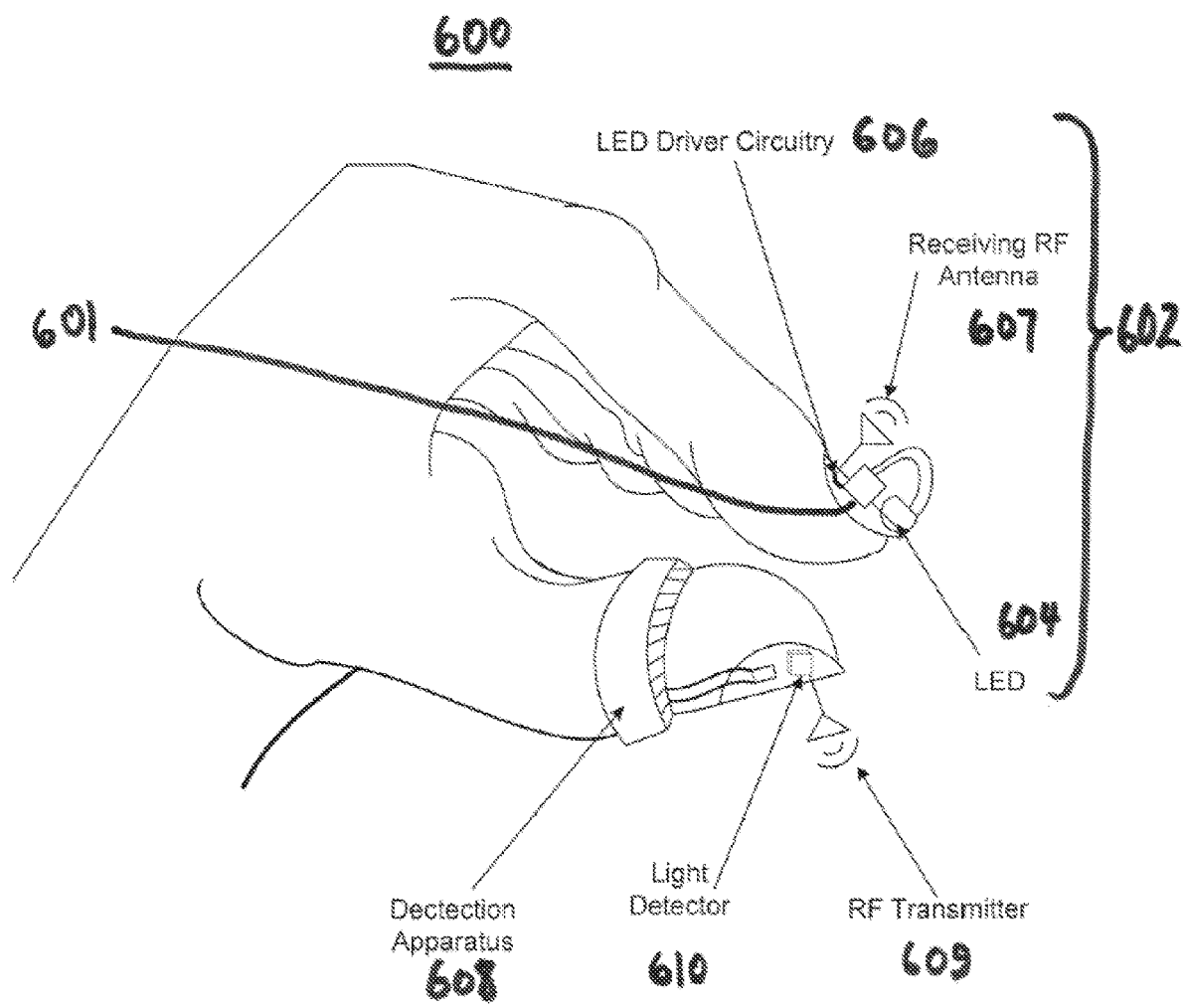
FIG. 6 is a schematic drawing of a pinch gesture performed with a gesture recognition and control system disposed on a user's hand, according to some embodiments.

FIG. 6 illustrates a pinch gesture performed using another gesture recognition and control system 600. System 600 includes a detection element 608 with an RF transmitter 609 and a light detector 610 mounted on one finger, and a signal element 602 comprising a receiving RF antenna 607 and an LED 604 (with LED driver 606) facing the fingernail 601 mounted on another finger. In some embodiments one or more of the other fingers are each configured with individual signal elements 602, and each LED driver 606 can be tuned to respond to a different RF frequency or modulated RF signal. The detection element 608 can continually alternate between sending an RF pulse which activates the respective LED 604 on each successive finger. If a particular finger is in range, the LED driver circuit 606 is activated and responds with a single light pulse, which travels through the sending finger and the receiving finger, to be detected by the light detector 610 on the detection element 608. This embodiment has the advantage of saving battery life on the LED driver circuits 606 mounted on each fingernail 601, allowing them to be less cumbersome and lighter (e.g., to be configured as cosmetic "snap on" fingernails).

Figure 7:
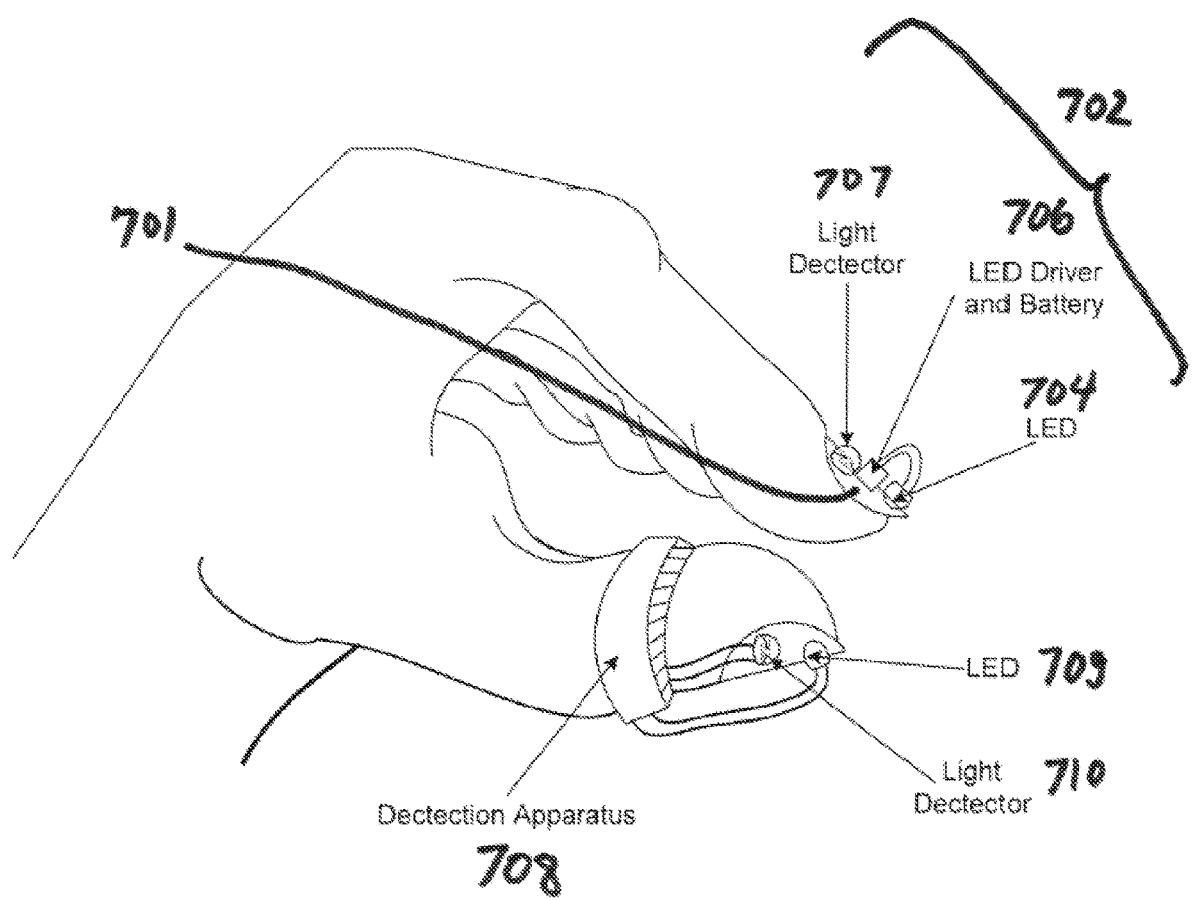
FIG. 7 is a schematic drawing of another pinch gesture performed with a gesture recognition and control system disposed on a user's hand, according to some embodiments.

FIG. 7 illustrates a pinch gesture performed using another gesture recognition and control system 700. In system 700, a detection element 708 with an LED 709 and a light detector 710 is disposed on one finger, and a signal element 702 with LED driver circuitry 706 comprising a light detector 707 and an LED 704 facing the fingernail is disposed on another finger. In this embodiment, the LED driver 706 can be tuned to respond to different light pulse patterns and frequencies. When the detection element LED 709 outputs light, it emits the light at a certain frequency, or in a specific frequency or pulse pattern. The LED driver 706 can be configured (in cooperation with the signal element light detector 707) to detect a unique frequency or frequency/pulse pattern of the light emitted by the detection element LED 709. In an embodiment wherein the other fingers are each configured with individual signal elements 702, the detection apparatus 708 can continually alternate between sending light pulses which would activate the signal element LED 704 on each respective finger. If a particular finger is in range, the signal element LED driver circuit 704 is activated and responds with a single light pulse, which travels through the sending finger and the receiving finger, to be detected by the light detector 710 on the detection element 708. This embodiment also has the advantage of saving battery life on the LED driver circuits 706 mounted on each fingernail, allowing them to be less cumbersome and lighter.

Various embodiments described herein may be realized using a plastic "snap on" fingernail configured with miniaturized components, e.g., a light detector (e.g., facing the fingernail), a surface mount miniature LED (e.g., facing the fingernail), a miniaturized LED driver, an antenna to relay output to an external receiver, a battery (such as a watch battery), and the like. The snap on fingernail may be produced using any suitable material as known in the art, with the components mounted on the surface using a suitable adhesive.

As noted above, using the gesture recognition and control systems described herein, gestures can be used to actuate an external device, such as a prosthetic limb. Embodiments described below also include gesture tracking and control systems that are worn on a user's sound (healthy, normal) hand in order to detect different grasp patterns or poses, which are used to control a powered prosthetic device.

Figure 8A:
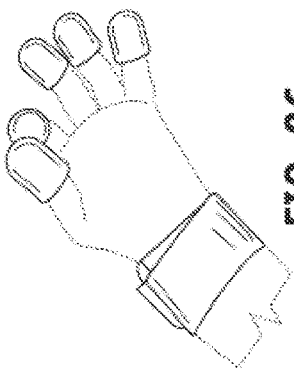
FIGS. 8A-8I are images of a gesture recognition and control system using conductive thimbles disposed on a user's hands, according to some embodiments.
Figure 8B:
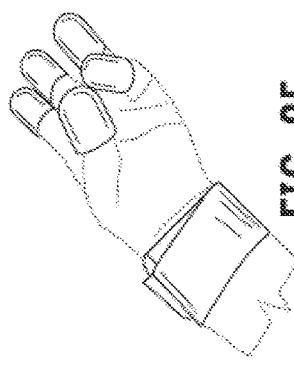
Figure 8C:
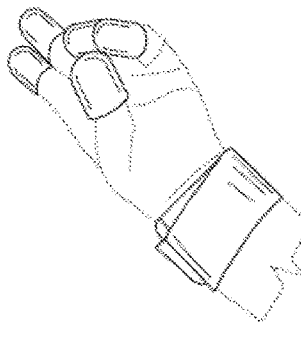
Figure 8D:
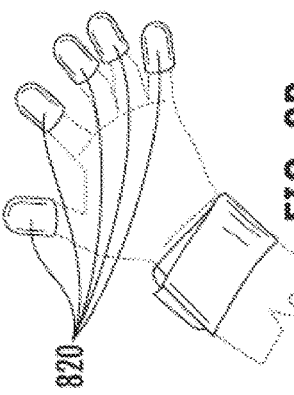
Figure 8E:
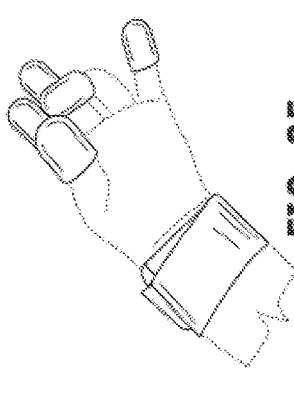
Figure 8F:
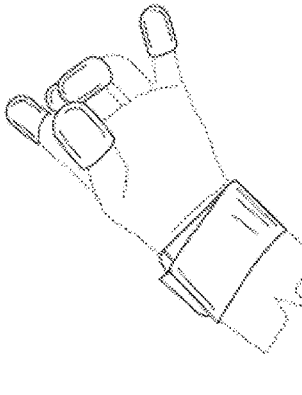
Figure 8G:
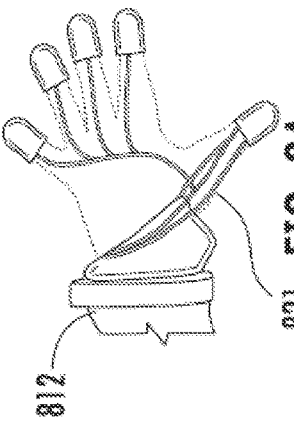
Figure 8H:
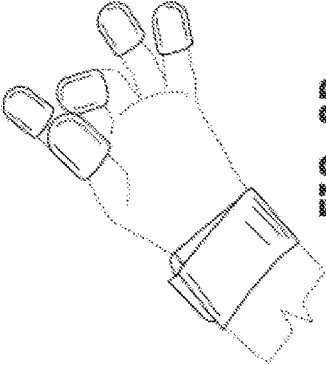
Figure 8I:
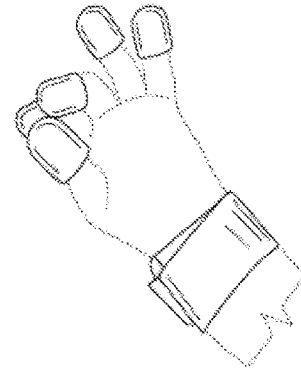

FIGS. 8A-8I illustrate a gesture tracking and control system 800, showing, inter alia, different gestures. System 800 comprises conductive thimbles 820, one worn on each finger, which are used to control a prosthetic device, such as a prosthetic limb. The thimbles 820 are formed with a conductive outer surface (e.g., a conductive metallic film). In some embodiments each of the thimbles 820 may be formed as a conductive metal 'cup' disposed onto an insulating material (e.g., a plastic, foam, or rubber layer with a cotton lining) configured to fit the user's fingers. The thimbles 820 are electrically coupled to a microcontroller board 812 (further described below). The electrical connections may be made via wires 821 coupled to the thimbles 820 using any suitable conventional connection means as known in the art. Contact between one or more fingers (each connected to an analog input on the microcontroller) and the thumb (connected to the +5V output of the microcontroller board) is interpreted as a gesture. Each of FIGS. 8C-8I illustrates a different gesture. Each gesture corresponds to a specific grasp pattern, not necessarily mirroring the pose of the gesture. That is, the gesture serves as an instruction to a controller to cause the prosthetic device to take on a specific grasp pattern corresponding to the specific gesture. Grasp pattern activation was tested (including the selection of "open" and "closed" forms of a given pattern) both with direct gestures, without relying on an EMG based input. FIGS. 8A and 8B do not illustrate gestures, but are provided to give a full view of the system components on all the fingers, on both sides of the hand.

Figure 9A:
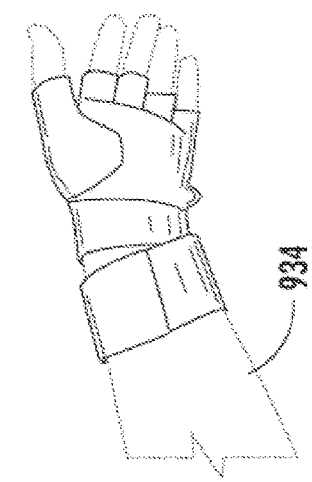
FIGS. 9A-9C are images of a glove-based recognition system, according to some embodiments.
Figure 9B:
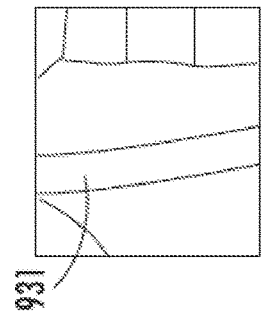
Figure 9C:
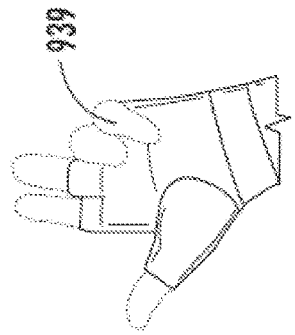

FIGS. 9A-9G illustrate a gesture tracking and control system 900. System 900 comprises a conductive glove 930 and thread 931 (the "conductive glove") to be worn on the healthy hand. The conductive glove 930 leaves the healthy fingers free for the performance of non-system-related tasks. The conductive glove 930 is suitable for being worn for extended periods of time. In one embodiment, the conductive glove 930 was constructed from a fingerless weightlifting glove by embroidering conductive thread touch pads 931 in the palm of the glove 930 and connecting them to snap connectors 932 sewn on the dorsal side of the glove 930. The conductive thread lines (not shown) going from the embroidered pads 931 to the snap connectors 932 were insulated with fabric affixed to the inside of the glove 930. (The conductive thread touch pads 931 are shown in FIGS. 9B and 9C, and the snap connectors 932 are shown in FIG. 9A.)

Figure 10:
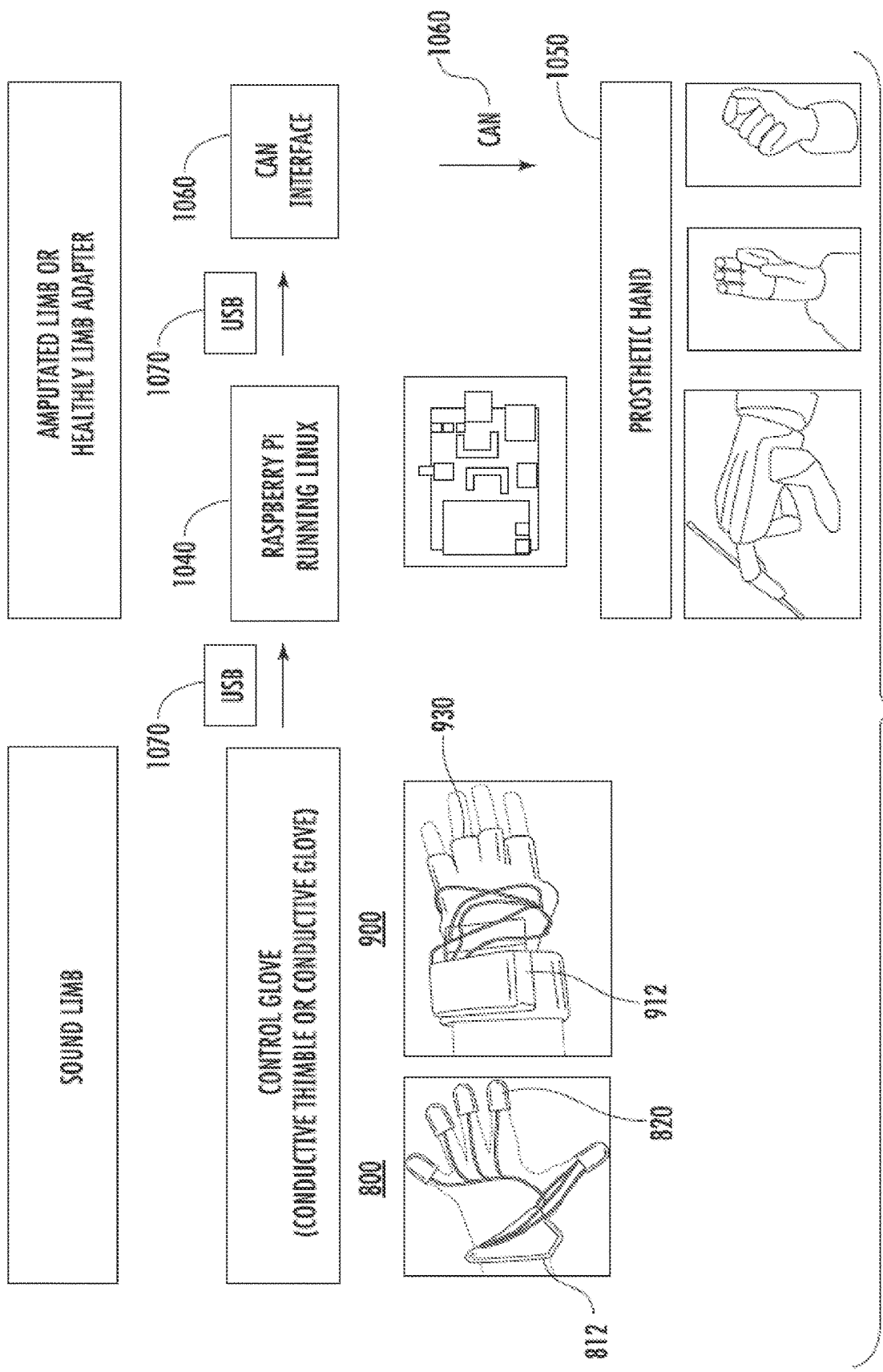
FIG. 10 is a schematic diagram of an operating hierarchy for a gesture recognition and control system, applicable to multiple types of such systems, according to some embodiments.

FIG. 10 illustrates an operating hierarchy for systems 800 and 900. As with the conductive thimble system 800, so too the conductive glove system 900 entails a microcontroller 912. Each of microcontroller 812 and microcontroller 912 may be, e.g., an Arduino® microcontroller. The thimble 820 or glove 930 is connected to the microcontroller board 812 or 912, respectively, running the appropriate software. The microcontroller 812, 912 interprets the input from the thimbles 820 or the glove 930 and creates commands, such as UNIX shell commands, which are communicated to a computer 1040 (e.g., a Raspberry Pi™ computer) disposed on the prosthetic device 1050, and which, in turn, control the prosthetic device 1050 via a Controller Area Network (CAN) interface 1060. Connections 1070 between microcontroller 812, 912, computer 1040, and interface 1060 may be made by any suitable connection means known in the art, e.g., Universal Serial Bus (USB).

Figure 9D:
FIGS. 9D-9G are images of hand gestures performed with the glove-based recognition system, according to some embodiments.
Figure 9E:
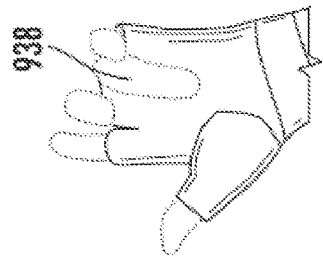
Figure 9F:
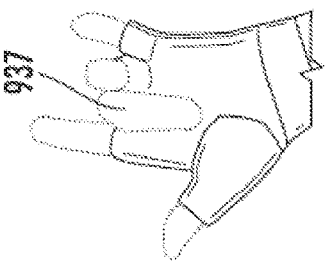
Figure 9G:
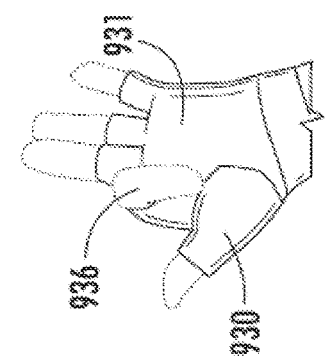

Returning to FIGS. 9A-9G, a contact pad (not shown; also referred to as a first electrically conductive pad) was embroidered on the inside of the glove 930 so that it makes contact with the skin and was connected to the +5V terminal 933 of the microcontroller 912 board via another snap connector 932 (see FIG. 9A). In operation, the user touches one of the conductive pads 931 (also referred to as a second electrically conductive pad) with a finger and completes the circuit causing a signal to be acquired by the A/D converter (of the microcontroller 932). The system identifies touch gestures from each fingertip while not registering any accidental gestures from objects that the user might be manipulating. The skin contact with the +5V terminal 933 may be further enhanced by connecting the terminal 933 to a gel electrode 934 designed for use with a Transcutaneous Electrical Neural Stimulator (TENS) system (Infiniti ELT 5050T) (FIG. 9B). The TENS electrode 934 is not strictly necessary, but it improves the signal-to-noise ratio, largely eliminating misclassified gestures. The output from the conductive pads 931 was sampled with the built-in 10 bit A/D converter of the ATmega 328 microcontroller 932 on the Arduino® board. FIGS. 9D-9G show example gestures that can be performed with the conductive glove 930. A gesture is performed by touching one or more fingers to the conductive thread pad 931 located on the palm of the glove 930. FIG. 9D shows the gesture of touching the index finger 936 to the pad 931, FIG. 9E shows the gesture of touching the middle finger 937 to the pad 931, FIG. 9F shows the gesture of touching the fourth finger 938 to the pad 931, and FIG. 9E shows the gesture of touching the fifth finger 939 to the pad 931. Other gestures are possible, including touching the pad 931 with more than one finger. Each gesture corresponds to a respective grasp pattern, i.e., the gesture is captured by microcontroller 912 and serves as an instruction to control the prosthetic device on the other hand to take on the grasp pattern.

In order to allow non-impaired volunteers to wear and test systems disclosed herein, a so-called healthy limb adapter was created. A prosthetic device mounted on the end of the limb adapter was used to test the systems. A suitable prosthetic device (Touch Bionics™ robo-limb) is produced by Touch Bionics Inc. (www.touchbionics.com). The limb adapter incorporates an Ottobock® Quick Connect ring (Otto Bock, Germany) attached via standard nuts and bolts via a custom 3D printed bracket attached to a plastic shell. The ring is disposed between the prosthetic hand and the shell. The shell was formed out of heat moldable thermoplastic (Worbla, USA) with a heat gun by using a plaster of Paris replica of the subject's arm as a template. Power and data wires were routed to the outside of the healthy limb adapter through a drilled hole. An armband (formed using Velcro®) is used to hold the circuit boards terminating a controller area network (CAN) cable and providing power, batteries, and a Kvaser® Leaf (Kvaser, USA) USB to CAN adapter. A Raspberry Pi™ embedded computer, which interprets the signals from the microcontroller to generate the CAN messages driving the prosthetic device, is also affixed to the armband. A USB cable was used to connect the tracking glove to the Raspberry Pi™ device on the healthy limb adapter.

In testing the embodiment implementations, for purposes of circuit design and software parameter specifications, the hand was treated as a 1 to 2 MΩ resistor. By touching the conductive pad with a bare fingertip, the circuit is completed, causing the A/D converter to see an increase in voltage. A touch classification algorithm was developed in order to classify touch events. For this, an algorithm using moving average and moving standard deviation was developed. The moving standard deviation is a method that is useful in various applications where the signal is noisy or the baseline is not stable. Further description of the classification touch algorithm, conductive thimbles, and conductive glove embodiments of the invention is found in: Oguz Yetkin et al., Control of a Powered Prosthetic Device via a Pinch Gesture Interface, University of Texas at Arlington, which is hereby incorporated herein by reference in its entirety. A copy of this paper is included as Appendix A in the provisional application to which the instant application claims priority. The instant inventors are co-authors of this paper.

The systems disclosed herein provide interfaces to control external devices, such as powered prosthetics. For implementation of the embodiments by unilateral amputees, the system's devices are worn on the user's sound hand to tele-operate the prosthetic device by mirroring the user's gestures. Some embodiments are also configured to allow the user to pose and lock the prosthetic device when independent hand movement of the healthy hand is desired. This feature allows the user to 'pause' the prosthetic to allow different, independent, motion with the sound hand, i.e., when the user wishes to use the sound hand for some purpose or task other than controlling the prosthetic device.

In this regard, other embodiments utilizing a glove implementation are provided. In one embodiment, Sparkfun Electronics® 2.2 flexion sensors (Spark Fun Electronics, Inc.) are sewn onto the glove fingers. A microcontroller (e.g., Arduino® Uno microcontroller) is also affixed to the glove using Velcro®. A sensor shield is also implemented with the microcontroller. The shield contains circuitry to pre-amplify the output from the piezoelectric sensors, along with buttons, potentiometers, and LED indicators for calibration without involving an external computer. The glove is also configured with a "pause" switch which can be actuated by pressing against the body or an object. The switch temporarily disables the mirroring functionality, allowing the user to perform independent manipulation with the sound hand. According to this embodiment, for example, a user may perform a bilateral mirrored task (such as carrying a box), then pause the prosthetic device in the given pose employed for the bilateral mirrored task, in order to perform a different manipulation (e.g., removing a bottle cap) with the sound hand.

The software and hardware architecture for this embodiment is similar to the configuration represented in FIG. 10. The software utilizes three components: a microcontroller, a standard UNIX BASH shell, and code running on a Raspberry Pi™ device which can open and close individual digits via the command line. The software running on the microcontroller composes a UNIX command to set the position of each digit and send it over the USB cable to the Raspberry Pi™. The Raspberry Pi™ conveys the command received from the serial port to the BASH command interpreter, invoking the software with the set arguments. In some embodiments, the software is configured to: issue the command to stop any movement that might be happening on the prosthetic device; issue the command to each digit to go to a desired/required position.

With further regard to this embodiment, an amplifier circuit may be employed for each flexion sensor. Since the flexion sensors display a high resistance value (which results in a small voltage change when the sensor is bent), with each one having a different associated range, potentiometers are used in the circuit to allow for individual adjustment of each sensor's output.

For testing purposes, this embodiment was also configured and operated using the healthy limb adapter described above. Further description of these embodiments is found in: Oguz Yetkin et al., Control of a Powered Prosthetic Hand via a Tracked Glove, University of Texas Arlington, flyer; Oguz Yetkin et al., Evaluation of Prosthetic Control via Hand and Gesture Tracking, University of Texas Arlington, paper; and in Oguz Yetkin et al., Control of a Powered Prosthetic Hand via a Tracked Glove, University of Texas Arlington, paper; all three of which are hereby incorporated herein by reference in their entirety. Copies of this flyer and both papers are included as Appendices B, C and D, respectively, in the provisional application to which the instant application claims priority. The instant inventors are co-authors of these papers and flyer.

Figure 11:
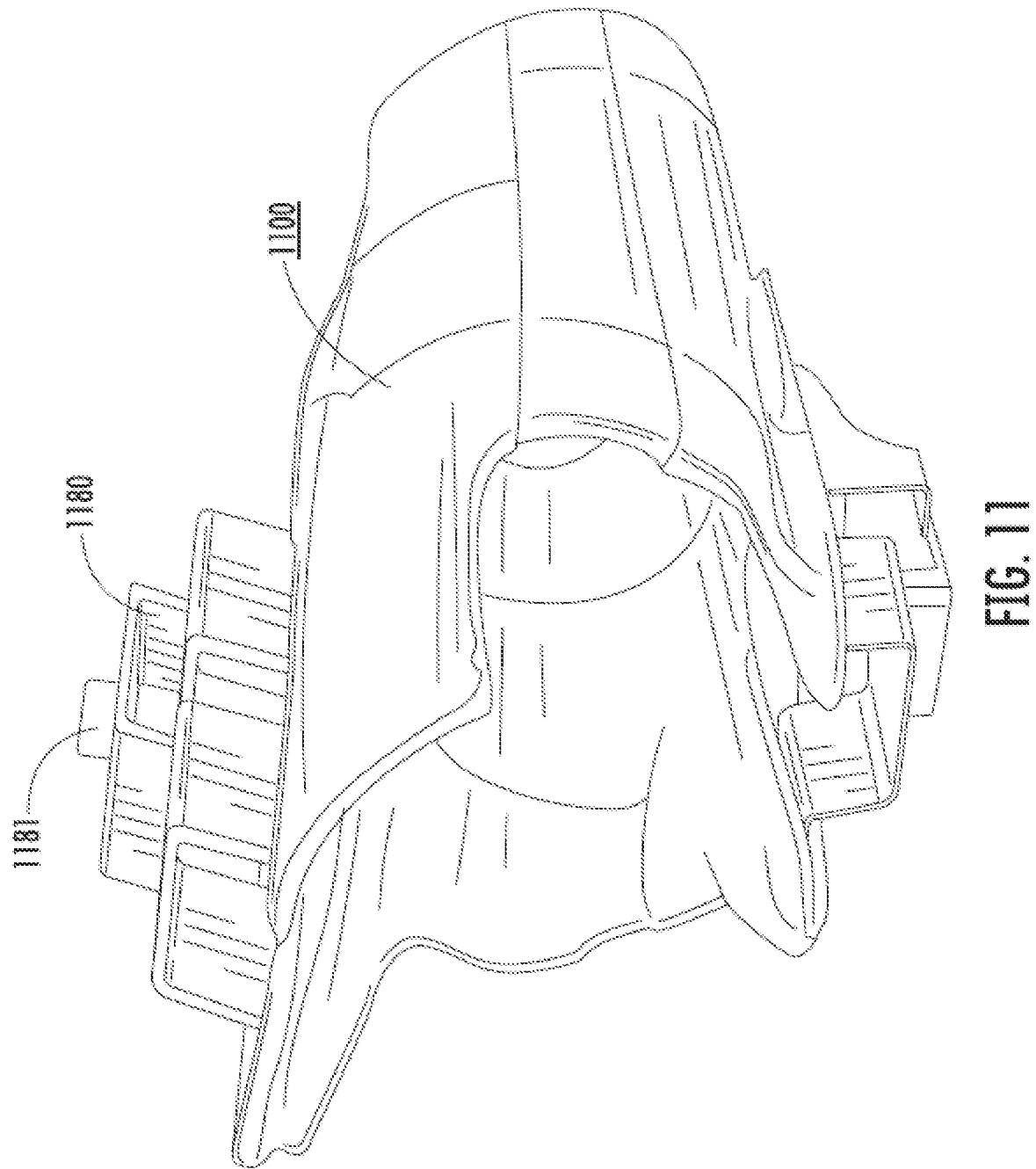
FIG. 11 is an image of a sleeve (socket) device, which may be used in a system for controlling an external device, according to some embodiments.

Some embodiments are implemented to facilitate the control and functionality of a powered prosthetic device (e.g., by trans-radial amputees) through the use of intra-socket force readings, combined with the pinch gesture glove or thimble embodiments disclosed herein. FIG. 11 illustrates a socket utilized in certain embodiments.

More specifically, FIG. 11 shows a custom, prosthetic trans-radial amputee socket 1100 produced for an able-bodied man. An alginate mold was created of the subject's dominant side lower arm, below the bicep, and a plaster cast was created from this mold. From this plaster cast, a socket 1100 was created by first wrapping the outside of the forearm in the socket material, thermoplastic, and then layering subsequent layers inside of the socket 1100. The hand flexion and extension of the forearm were identified on the subject, located on the anterior and posterior sides of the forearm. These points were marked and corresponding positions within the socket 1100 were identified. Above these positions, custom designed sensor housings 1180 were mounted, as shown in FIG. 11. These housings secure piezo-resistive force sensors 1181 (e.g., FlexiForce® A201 piezo-resistors) for interaction detection. As the user flexes the arm muscles, the carpi flexor and carpi extensor muscles change in volume. This volume change is detected as a force applied to the inside of the socket 1100 and is detected by the piezo-resistive sensor 1181.

By implementing the piezo-resistive sensors in a prosthetic device (e.g., a prosthetic hand) such that skin contact is made, as the user causes muscle deformation of the forearm during flexion and extension activities, the sensors detect the changes in force and pressure. This technique is referred to as Force Myography (FMG). Embodiments disclosed herein include the use of such FMG interfaces used to control functionality of powered prosthetic devices through the use of intra-socket force readings. Embodiments disclosed herein also entail the use of the Pinch Gesture devices disclosed herein, in combination with the use of intra-socket pressure sensors.

Figure 12:
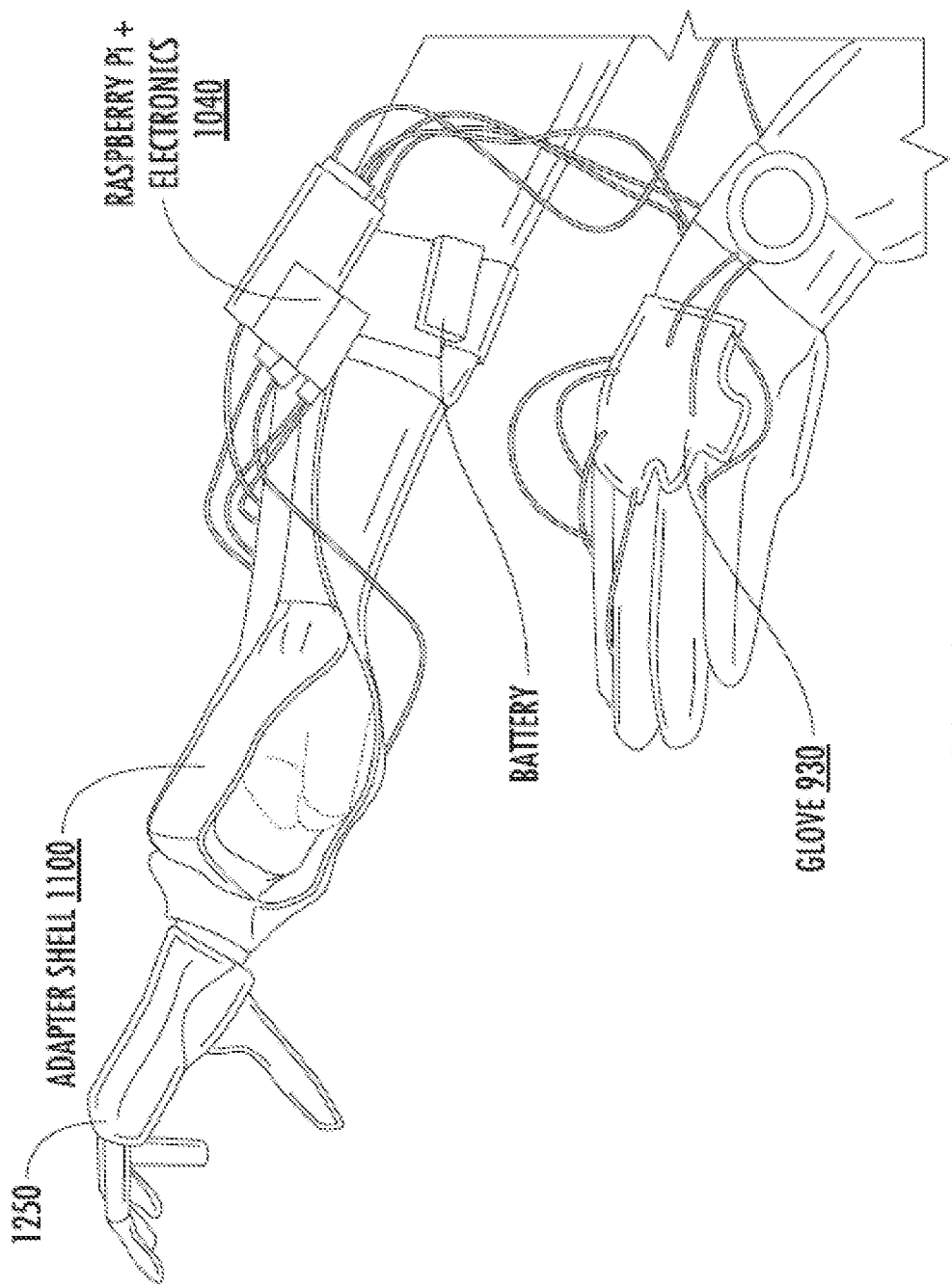
FIG. 12 is an image of a gesture recognition and control system, according to some embodiments.

FIG. 12 shows an embodiment combining the intra-socket system and the pinch gesture glove system. This combination allows control and activation via several modalities, including the use of gestures to select between grasp patterns, use of hand tracking to tele-operate the prosthetic hand by mirroring the sound hand, activation of selected grip patterns via intra-socket pressure, and a method of turning gesture-based control on and off at will. As seen in FIG. 12, a healthy limb adapter, similar to that described above, was used to test this embodiment. A Touch Bionics i-Limb™ ultra-powered prosthetic hand was configured to demonstrate possible grip configurations. Each of six degrees of freedom are independently controllable, using an open-loop controller. The combination system of FIG. 12 includes, on the healthy hand, conductive glove 930 (for brevity, the components of glove system 900 are not individually mentioned here), and, on the other arm, a prosthetic hand 1250, a socket 1100, and a Raspberry Pi™ computer 1040 to control the prosthetic hand 1250 (for brevity, other elements on the limb adapter, described above, are not individually mentioned here.)

A prosthetic device configured with the piezo-resistive force sensors allows the user to control the opening, closing, and stopping of the motion of the powered prosthetic device. In some embodiments, user interaction with this embodiment involves the selection of a grip-type via an application stored on a mobile device or chosen by "scrolling through" pre-programmed grip patterns using a surface EMG as a scroll switch. Opening and closing of the grip is completed via a predefined input through the surface EMG. Alternate methods of grip selection and control algorithms for implementation of embodiments of the invention are described in: Joe Sanford et al., A Novel EMG-Free Prosthetic Interface System Using Intra-Socket Force Measurement and Pinch Gestures, University of Texas Arlington; Joe Sanford et al., Concurrent SEMG and Force Myography Classification During times of Prosthetic Socket Shift and User Fatigue, IEEE Journal of Transactions on Biomedical Engineering, February 2016; and Joe Sanford et al., Surface EMG and Intra-Socket Force Measurement to Control a Prosthetic Device, University of Texas Arlington; all three of which are hereby incorporated herein by reference in their entirety. Copies of these papers are included respectively in Appendices E, F and G of the provisional application to which the instant application claims priority. The instant inventors are co-authors of these papers.

Turning to FIG. 13, another embodiment of a fingernail-worn device for detecting pinch gestures and communicating with the prosthetic device is shown. Similar to some other embodiments described herein, this configuration detects the relative position of fingers to each other by measuring light transmitted via tissue. Fingernail mounted signal/detection element or sensor holders 1305 for an LED 1304 and a photodiode 1307 were modeled in SolidWorks® and 3D printed using a filament extruder. A high powered 639 nm LED 1304 and a broad spectrum photodiode 1307 were friction fit into the sensor holder 1305. Both the LED 1304 and the sensor 1307 on each sensor holder 1305 are soldered to thin wires.

Figure 14A:
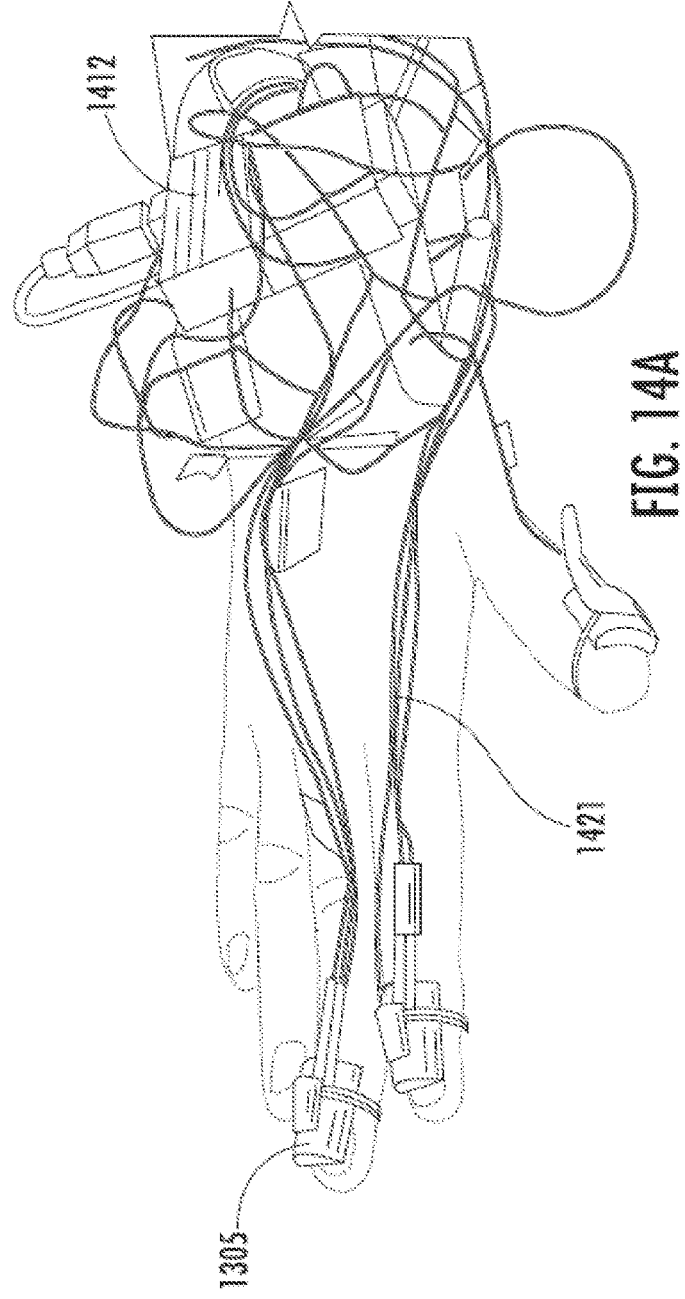
FIG. 14A-14D are images of a gesture recognition and control system disposed on a user's hand, according to some embodiments.
Figure 14D:
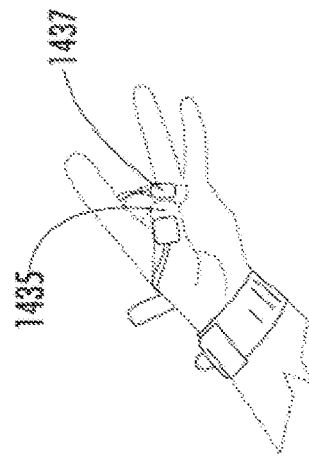
Figure 14C:
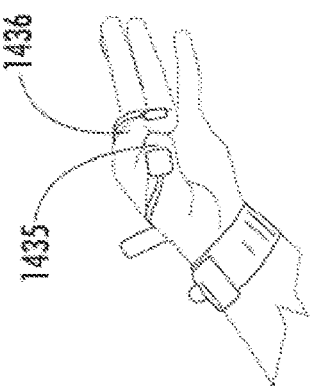
Figure 14B:
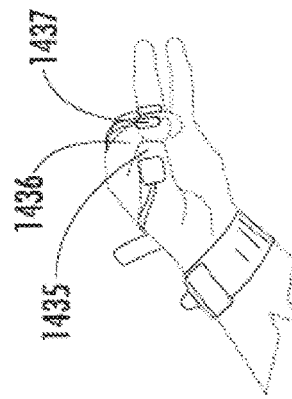

FIGS. 14A-14D illustrate a system 1400 using the fingernail-worn devices of FIG. 13, the system being configured with one thumb sensor 1305 and two fingernail sensors 1305. The wiring 1421 is connected via DuPont® connectors to a wrist worn microcontroller 1412 board. The microcontroller 1412 board is constructed out of a Velcro® wristband, an Arduino® Genuino microcontroller board, and a custom Arduino® shield with circuitry to drive the LEDs 1304 and read the input from the photodiodes 1307 shown in FIG. 13. These embodiments take advantage of the fact that certain wavelengths of light travel through tissue. Since a person's fingers generally have a similar index of refraction, the light signal changes as the fingers come into physical contact and form a waveguide for the light, as well as when the fingers are breaking contact. Light transmission between the fingers is greatly enhanced when the fingers are brought together physically. This change in signal enhancement provides for easier transmission from a fingernail to a thumbnail, allowing light directed at a fingernail to be detected at a sensor aimed at the thumbnail. While FIG. 14A shows the system as a whole most clearly, each of FIGS. 14B-14D shows a respective one of three different sample pinch gestures that can be performed with this system. In FIG. 14B, the pinch gesture is bringing the index finger 1436 and the middle finger 1437 into contact with the thumb 1435; in FIG. 14C, the pinch gesture is bringing the index finger 1436 into contact with the thumb 1435; and in FIG. 14D, the pinch gesture is bringing the middle finger 1437 into contact with the thumb 1435.

The embodiment of FIG. 13 was used to detect touch events. For this detection method of the invention, each detection cycle is broken into detection windows of a specific duration (e.g., 200 ms). Each finger is assigned a characteristic response time (r1, r2, r3, r4). These times are chosen to be smaller than the window duration (e.g., 25 ms, 40 ms, 57 ms, 75 ms, etc.) but larger than pulse duration (e.g., 5 ms). During each detection window, the LEDs are flashed in succession. Simultaneously, the microcontroller reads the light intensity on the photodiode and looks for peak intensities corresponding to the response times (r1, r2, etc.). Detection of such a peak is counted as a touch event.

In some embodiments, the configuration depicted in FIG. 13 and FIGS. 14A-14D is modified slightly to allow the sensors on each finger to be controlled by their own untethered microcontroller. These embodiments are similar in operation to the time-based detection embodiments described in the preceding paragraph except that an interrogation pulse is sent from the thumb to the sensors mounted on each fingernail. If the sensor on the fingernail detects a light peak, it responds after a characteristic response time (e.g., r1 for index finger, r2 for middle finger, r3 for ring finger, r4 for little finger). Nominal values of, e.g., 25, 40, 57, and 75 ms can be chosen. The sensor on the thumb detects the response and registers a touch event if one or more peaks are detected within response times corresponding to a finger. These embodiments have the advantage of allowing fingernail based sensors to be completely untethered and manufactured inexpensively, as all they need to do is to respond to a light pulse. This furthermore increases battery life, since the fingernail mounted sensors only have to respond to a pulse if the fingers are in contact.

The time-domain based embodiments of FIG. 13 and FIGS. 14A-14D may be prone to noise, and an assumption can be made that the signal from the LED will be the brightest light pulse detected by the photodiode during the detection window. Thus a bright LED may be used to ensure better performance. Alternative embodiments may be implemented using a Fast Fourier transform (FFT) involving placing LEDs flashing in different frequencies on each fingernail, and detecting the light traveling through both fingers when the pinch gesture is performed. This greatly simplifies the design of the fingernail mounted devices, as no microcontroller is needed on the four fingernails.

Signal processing for embodiments can be implemented via a Matlab® code written to take a vector of time domain data sampled from the photodiode, and return a vector containing (time, frequency) pairs where the "frequency" represents maximum frequency within a short window of time. This is accomplished through a sliding window approach with a window length of 20 samples, for example. In one embodiment, such code was used ("frequency_detector"). The frequency_detector eliminates all frequencies outside the desired frequency range.

In order to test the frequency_detector code and to select the most optimal frequency pairs which can be detected by the Arduino® microcontroller board, simulations were run on different frequency pairs ranging from 10 to 400 Hz. To enhance the accuracy of frequency prediction, both random and 60 Hz noise were added. The most optimal frequencies were chosen based on RMS distance calculations between normalized "ground truth" and result vectors. Further description of these embodiments of the invention is found in: Oguz Yetkin et al., An extremely lightweight fingernail worn prosthetic interface device, University of Texas Arlington, which is hereby incorporated herein by reference in its entirety. A copy of this paper is included as Appendix "H in the provisional application to which the instant application claims priority. The instant inventors are co-authors of this paper.

After reading the description presented herein, it will become apparent to a person skilled in the relevant arts how to implement embodiments disclosed herein using computer systems/architectures and communication networks other than those described herein. It will also be appreciated by those skilled in the relevant arts that various conventional and suitable materials and components may be used to implement the embodiments of the invention disclosed herein.

In light of the principles and example embodiments described and illustrated herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise or so dictated by the description herein. This disclosure may include descriptions of various benefits and advantages that may be provided by various embodiments. One, some, all, or different benefits or advantages may be provided by different embodiments.

Similarly, although example methods or processes have been described with regard to particular steps or operations performed in a particular sequence, numerous modifications could be applied to those methods or processes to derive numerous alternative embodiments of the present invention. For example, alternative embodiments may include methods or processes that use fewer than all of the disclosed steps or operations, methods or processes that use additional steps or operations, and methods or processes in which the individual steps or operations disclosed herein are combined, subdivided, rearranged, or otherwise altered. Similarly, this disclosure describes one or more embodiments wherein various operations are performed by certain systems, applications, module, components, etc. In alternative embodiments, however, those operations could be performed by different components. Also, items such as applications, module, components, etc. may be implemented as software constructs stored in a machine accessible storage medium, such as an optical disk, a hard disk drive, etc., and those constructs may take the form of applications, programs, subroutines, instructions, objects, methods, classes, or any other suitable form of control logic; such items may also be implemented as firmware or hardware, or as any combination of software, firmware and hardware, or any combination of any two of software, firmware and hardware. The term "processor" or "microprocessor" may refer to one or more processors.

Further, the methods set forth herein may also be implemented as an article of manufacture embodiment, wherein an article of manufacture comprises a non-transitory machine-accessible medium containing instructions, the instructions comprising a software application or software service, wherein the instructions, when executed by the machine, cause the machine to perform the respective method. The machine may be, e.g., a processor, a processor-based system such as the systems described herein, or a processor-based device such as the user interface devices described herein.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A system, comprising:
a signal element configured to generate a signal;
a fingernail mount configured to secure the signal element on a fingernail of a first finger of a user such that the signal element remains on the fingernail of the first finger of the user while the user performs a gesture; and
a detection element configured for disposal on a second finger of a user, and configured to detect a signal generated by the signal element, wherein the signal indicates that the user has performed the gesture using the first finger and the second finger of the user;
wherein the detection element comprises a circuit configured to distinguish the signal from the signal element from a plurality of other signals from other signal elements disposed on a plurality of other fingers of the user; and
wherein the circuit is configured to distinguish the signal from the signal element from the plurality of other signals from the other signal elements by measuring signal intensity of the signal element as acquired by a combination of antennas and determining a position of the signal element relative to a plane of a palm of the user.

2. The system according to claim 1, wherein the detection element is further configured to detect a characteristic of the signal, the characteristic of the signal indicative of a characteristic of the gesture.

3. The system according to claim 2, wherein the characteristic of the signal comprises an RFID tag ID, and wherein the detection element is configured to distinguish the first finger from a plurality of other fingers based on the RIFD tag ID.

4. The system according to claim 2, wherein the characteristic of the signal comprises a signal intensity, strength, phase, or amplitude, or change therein.

5. The system according to claim 2, wherein the characteristic of the signal comprises a resonant frequency of a circuit transmitting or generating the signal.

6. The system according to claim 2, wherein the characteristic of the signal comprises a frequency of the signal.

7. The system according to claim 1, wherein the signal element comprises an RFID tag, and wherein the detection element comprises an RFID antenna.

8. The system according to claim 1, wherein the signal element comprises an LC circuit.

9. The system according to claim 1, wherein the signal element comprises a resonator and the receiver element is configured to distinguish the signal element based on a resonance frequency.

10. The system according to claim 9, wherein the resonator comprises an LC tank circuit.

11. The system according to claim 9, wherein the resonator comprises an RFID circuit.

12. The system according to claim 9, wherein the resonator comprises a microcontroller circuit configured to respond with a specified signal unique to the user's first finger or second finger.

13. The system according to claim 1, wherein the signal indicates that a sign language gesture has been performed using at least the first finger and the second finger of the user.

14. A system. comprising:
a signal element configured to generate a signal;
a fingernail mount configured to secure the signal element on a fingernail of a first finger of a user such that the signal element remains on the fingernail of the first finger of the user while the user performs a gesture;
a detection element configured for disposal on a second finger of a user, and configured to detect a signal generated by the signal element, wherein the signal indicates that the user has performed the gesture using the first finger and the second finger of the user; and
a controller configured to control a prosthetic device based on the signal detected by the detection element.

15. The system according to claim 14, wherein the control of the prosthetic device causes the prosthetic device to perform an action or a movement corresponding to the gesture.

* * * * *